United States Patent [19]

Baba et al.

[11] Patent Number: 4,643,757
[45] Date of Patent: Feb. 17, 1987

[54] HERBICIDAL 4-BENZOYL-1-METHYL-5-HYDROXYPYRAZOLES

[75] Inventors: Masatoshi Baba; Norio Tanaka, both of Funabashi; Takasi Ikai; Tsutomu Nawamaki, both of Shiraoka; Masaji Matsunaga, Tokyo, all of Japan

[73] Assignee: Nissan Chemical Industries, Ltd., Tokyo, Japan

[21] Appl. No.: 735,656

[22] Filed: May 20, 1985

[51] Int. Cl.⁴ .................. A01N 43/56; A01N 57/16; C07D 231/20; C07F 9/65
[52] U.S. Cl. .......................... 71/86; 71/87; 71/92; 548/116; 548/367; 548/377
[58] Field of Search ............... 548/367, 377, 116; 71/92, 86, 87

[56] References Cited

U.S. PATENT DOCUMENTS 4,063,925 12/1977 Konotsune et al. ............ 548/367
4,230,481 10/1980 Nishiyama et al. ............. 548/377

FOREIGN PATENT DOCUMENTS 172476 9/1984 Japan ..................... 548/377

OTHER PUBLICATIONS

Chem Abst., 103, 2154x (1985).
Chem Abst. 103, 2153w (1985).
Chem Abst. 103, 2152v (1985).
Chem Abst. 102, 24625h (1985).
Chem Abst. 102, 220872a (1985).
Chem Abst. 101, 211138t (1984).
Chem Abst. 100, 121061n (1984).

*Primary Examiner*—Richard A. Schwartz
*Assistant Examiner*—Kurt G. Briscoe
*Attorney, Agent, or Firm*—Quaintance, Murphy & Presta

[57] ABSTRACT

Pyrazole derivatives, selective herbicidal compositions containing said derivatives and the use of said derivatives are provided. The pyrazole derivatives having selective herbicidal activity are represented by the formula I:

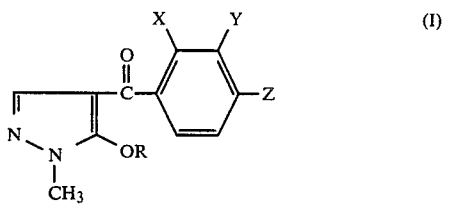

wherein,

X denotes a halogen, nitro or methanesulfonyl,
Y denotes hydrogen, a lower alkyl or a halogen,
Z denotes a halogen or methanesulfonyl, and
R denotes hydrogen; an organic acid residue; a lower alkynyl; a lower alkyl or a lower alkenyl which may be substituted by a halogen, hydroxy, cyano or an alkoxycarbonyl; or a benzyl which may be substituted by a halogen, nitro or a lower alkyl.

12 Claims, No Drawings

HERBICIDAL 4-BENZOYL-1-METHYL-5-HYDROXYPYRAZOLES

BACKGROUND OF THE INVENTION (1) Field of the Invention

The present invention relates to novel pyrazole derivatives and selective herbicidal composition containing as an active ingredient one or two or more of said pyrazole derivatives.

(2) Description of the Prior Art

Hitherto, extensive researches and development on herbicides have been conducted for long years to provide varieties of herbicides for practical use. These herbicides have contributed to saving the labors for controlling weeds and to increasing production of agricultural and horticultural crops.

Yet, it is still required at present to develop novel drugs having more superior herbicidal characteristics. Especially as to agricultural and horticultural herbicides, it is desirable that they selectively control intended weeds with a lower dosage without adversely effecting on cultivated crops. However, the drugs which have been already known do not necessarily exhibit such favorable herbicidal characteristics.

The present inventors have found, in the course of researches on herbicidal characteristics of various organic compounds to develop useful herbicides, that the compounds of the formula (I) given below exhibit excellent herbicidal action against true grasses (true grasses and umbrella plants) and various broadleaf weeds without showing substantial adverse effects on useful crops such as cultivated crops of, for example, corn and sorghum, and, thus, completed the invention.

SUMMARY OF THE INVENTION

An object of the present invention is to provide a novel pyrazole derivative having selective herbicidal action against weeds and grasses.

Another object of the invention is to provide a selective herbicidal composition containing said derivative as an active ingredient.

Other object of the invention will be apparent from the description below.

The pyrazole derivatives according to the present invention are represented by the following formula I:

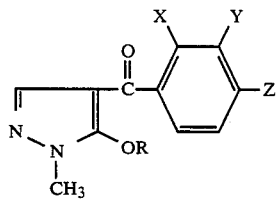

(I)

wherein,
X denotes a halogen, nitro or methanesulfonyl,
Y denotes hydrogen, a lower alkyl or a halogen,
Z denotes a halogen or methanesulfonyl, and
R denotes hydrogen; an organic acid residue; a lower alkynyl; a lower alkyl or a lower alkenyl which may be substituted by a halogen, hydroxy, cyano or an alkoxycarbonyl; or a benzyl which may be substituted by a halogen, nitro or a lower alkyl.

The chemical structural characteristics of these compounds reside in that 3-position of the pyrazole ring is unsubstituted (i.e. hydrogen atom).

DETAILED DESCRIPTION OF THE INVENTION

The halogen in the formula I generally means fluorine, chlorine, bromine or iodine atom, and preferably chlorine or bromine atom.

The halogen as X is preferably chlorine or bromine, and more preferably chlorine.

The halogen as Y is preferably chlorine or bromine.

The halogen as Z is preferably chlorine or bromine.

The halogen on the lower alkyl defined for R is preferably fluorine.

The halogen on the benzyl defined for R is preferably chlorine.

The lower alkyl as R or a moiety of R (on the benzyl defined for R) is a straight or branched alkyl usually having 1 to 4 carbon atoms and is preferably methyl, ethyl, n-propyl or i-propyl.

The lower alkenyl as R is a straight or branched alkenyl having 1 to 4 carbon atoms and is preferably allyl, 2-chloro-2-propenyl or 2-bromo-2-propenyl.

The lower alkynyl as R is a straight or branched alkynyl having 1 to 4 carbon atoms and is preferably 2-propynyl.

The alkoxy as a moiety of the alkoxycarbonyl is a straight or branched alkoxy having 1 to 4 carbon atoms, and is preferably methoxy, ethoxy or propoxy.

The organic acid residue as R includes methanesulfonyl, p-toluenesulfonyl, benzoyl, tert-butoxycarbonyl, acetyl, cyclohexylcarbonyl, cinnamoyl, acryloyl, phenoxyacetyl, ethoxycarbonyl, N,N-dimethylcarbamoyl, N,N-dimethylsulfamoyl, benzenesulfonyl, trifluoromethanesulfonyl, diethylphosphoryl or diethylthiophosphoryl and is preferably methanesulfonyl or p-toluenesulfonyl.

The important compounds according to the present invention include the following compounds:

(1) Compounds of the formula IA:

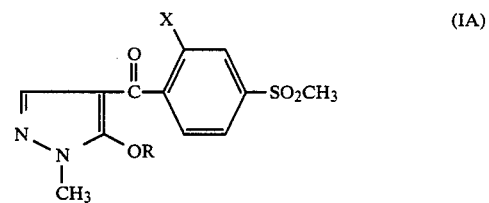

(IA)

wherein, X denotes a halogen, and R denotes hydrogen; an organic acid residue; a lower alkyl; a lower alkenyl; a lower alkynyl; a lower alkyl or a lower alkenyl each substituted by a halogen, hydroxy, cyano or alkoxycarbonyl; or a benzyl which may be substituted by a halogen, nitro or a lower alkyl.

(2) Compounds of the formula IB:

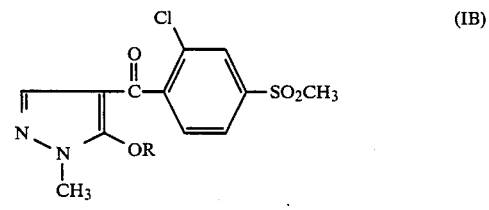

(IB)

wherein, R denotes hydrogen, methanesulfonyl or p-toluenesulfonyl, benzyl, propagyl or cyanomethyl.

The compounds according to the present invention exhibit strong herbicidal activities when used for soil-treatment and soil mixing-treatment or post emergence treatment; no practical damage or phytotoxity is observed at all with respect to cultivated crops such as corn, maize, *Sorghum bicolor* (sorghum), etc. by either the soil-treatment or soil mixing-treatment or post emergence treatment with these compounds. The compounds of the invention exhibit highly selective activities and, thus, are extremely useful for controlling weeds during the cultivation of crops. Namely, the compounds exhibit strong herbicidal activity against harmful weeds which grow during cultivation of corn and sorghum, such as *Echinochloa crus-galli* (barnyardgrass), *Amaranthus ascendens* (pigweed), *Polygonum nodosum* (smartweed), *Xanthium strumarium* (cocklebur), *Abutilon theophrasti* (velvet leaf), *Cyperus rotundus* (purple nutsedge), *Cyperus esculantus* (yellow nutsedge), etc. Particularly, herbicidal activity against nutsedges is markedly high and very unique. Hitherto have been used during cultivation of corn and sorghum a triazine herbicide, atrazine, or acid anilide herbicides, alachlor and metholachlor. However, atrazine exhibits low activity against true grasses and very low activity against nutsedge although it has a high activity against broadleaf weeds. On the other hand, alachlor and metholachlor exhibit low activity against broadleaf weeds and extremely insufficient activity against nutsedge although they have a high activity against true grasses. Thus, it has been difficult to destroy all kinds of weeds by a single treatment with a chemical.

The present inventors have found, after extensive researches on herbicidal compounds, the present compounds which exhibit activity against varieties of weeds and, especially, remarkably high activity against perennial weeds, nutsedge, which has been difficult to control among these weeds. Thus, the present inventors have completed the invention. The compounds according to the present invention are advantageous because they do not damage corn and sorghum at all and, thus, they can be used safely.

Hitherto, there have been known some pyrazole derivatives having herbicidal activity. For example, there is described in Japanese Patent Publication No. Sho. 54-36648 and Japanese Laid-open Patent Publication No. Sho. 54-41872 that 4-benzoyl derivatives are useful as a herbicide.

Among these pyrazole derivatives, however, only pyrazolate having the formula below (Compound A) is used practically and commercially as an active ingredient of a herbicide as far as the present inventors' knowledge is concerned.

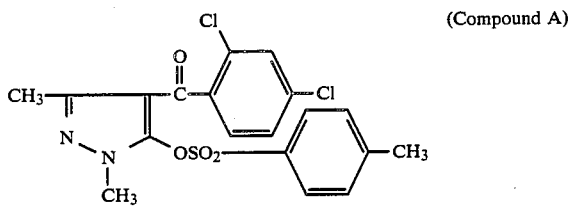
(Compound A)

All the pyrazole derivatives disclosed in the above mentioned Japanese Laid-open Patent Publication No. Sho. 54-41872 is substituted by methyl (CH$_3$) at 3-position of the pyrazole ring.

The majority of the pyrazole derivatives disclosed in the above mentioned Japanese Patent Publication No. Sho 54-36648 have a lower alkyl group at 3-position of the pyrazole ring and the substituent at 5-position thereof is —OH, —SH, a salt thereof or an ester with a specified organic acid. Among these pyrazole derivatives, only the following compound is exemplified as a pyrazole derivative having hydrogen atom at 3-position of the pyrazole ring:

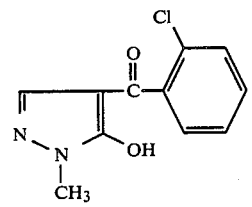

(hereinafter referred to as Compound B).

The Compound B, however, is inferior to the commercially available Compound A in herbicidal activity as apparent from the biological test data in the Japanese Patent Publication No. Sho. 54-36648.

The present inventors have confirmed that the compounds according to the invention have far superior herbicidal activity to Compounds A and B by conducting comparative tests of these compounds.

In spite of the facts that a number of pyrazole derivatives have been hitherto synthesized and the herbicidal activity tests thereof have been conducted, there has not been found a pyrazole derivative except the above-mentioned Compound B that has hydrogen atom at 3-position of the pyrazole ring.

This is because it has been very difficult to synthesize pyrazole derivatives having hydrogen atom at 3-position of the pyrazole ring while it has been relatively easy to synthesize pyrazole derivatives substituted by, for example, an alkyl, etc. at 3-position of said ring, and, moreover, because the former derivatives have been believed to be less active in herbicidal action than the latter alkyl derivatives and thus less practical than the latter ones.

The present inventors have made extensive researches on the pyrazole derivatives having hydrogen atom at 3-position of the pyrazole ring and have found a process for readily preparing such derivatives. Moreover, the present inventors have researched on the substituents at 5-position of the pyrazole ring and have unexpectedly found that the compounds of the formula (I) according to the present invention exhibit remarkably strong herbicidal action against true grasses and broadleaf weeds, as well as against nutsedges but are highly safe for corn and sorghum. Also the present inventors have found that such compounds exhibit extremely excellent properties as a herbicide to be used in a field. Moreover, the present inventors have found that these compounds not only exhibit high herbicidal activity against harmful weeds in a paddy field such as *Echinochloa crus-galli* (barnyardgrass), *Monochoria vaginalis, Lindernia pyxidaria, Rotala indica, Sagittaria pygmaea* and the like, but also have markedly high herbicidal activity against the weeds which have not been easily controlled, such as *Cyperus serotinus, Scirpus hotarui* and *Eleocharis kuroguwai.*

The superior effects on *Cyperus serotinus* etc. are brought about only by the chemical structure of pyrazole derivatives having hydrogen atom at 3-position of the pyrazole ring. It is also necessary, to provide such effects, that the benzoyl group on the pyrazole ring is substituted both at 2-position and 4-position of the benzyl ring.

Thus, the compounds according to the present invention exhibit remarkably high effects on perennial weeds such as *Cyperus serotinus* and *Eleocharis kuroguwai* which have not been easily controlled and against which no useful herbicide has been developed. The compounds according to the invention exhibit extremely excellent properties as a herbicide for a paddy field.

The compounds according to the present invention can be readily synthesized according to, for example, the following reaction:

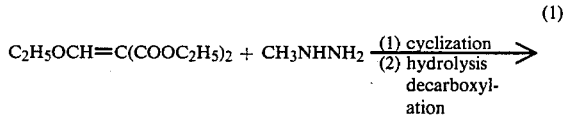

(1)

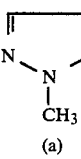

(a)

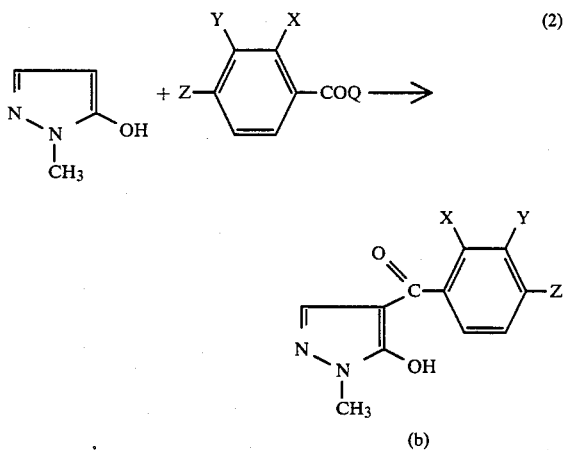

wherein, Q denotes a halogen or hydroxyl group, and X, Y and Z have the same meanings as defined in the formula (I).

Moreover, the Compound (b) can be readily converted to an appropriate organic acid ester through condensation reaction with an appropriate organic acid halide according to a conventional method.

Reaction (1) represents a reaction series comprising (i) synthesizing 4-carboethoxy-5-hydroxy-1-methyl-pyrazole from an ethoxymethylene malonate ester and methylhydrazine through cyclization reaction, followed by (ii) hydrolyzing and decarboxylating the resulting compound to obtain 5-hydroxy-1-methyl-pyrazole.

The compound (b) can be readily synthesized from the Compound (a) according to the Reaction (2). For example, compounds (b) may be prepared by reacting compound (a) with a substituted benzoyl halide in an inert solvent in the presence of a dehydrohalogenating agent, preferably such as sodium hydroxide, potassium hydroxide, sodium carbonate or triethylamine to produce the corresponding esters and then effecting rearrangement of the esters to obtain the compounds (b). As the solvent for the esterification reaction may be used, for example, organic solvents such as dioxane, acetonitrile, benzene, toluene or chloroform alone or in combination with each other or with water, namely two phase systems such as water-toluene, water-chloroform and the like.

The rearrangement reaction can be readily proceeded without any solvent or in a solvent inert to the reaction (desirably dioxane, acetonitrile and the like) in the presence of a Lewis acid such as aluminum chloride, tin chloride, zinc chloride, etc., or a base such as calcium hydroxide, potassium carbonate, sodium carbonate, etc.

The process for production of the compounds according to the invention will be illustrated specifically by way of the following examples. It should be noted that these examples are only illustrative and that the invention is not restricted to these examples.

SYNTHESIS EXAMPLE 1

Synthesis of 1-methyl-5-hydroxypyrazole

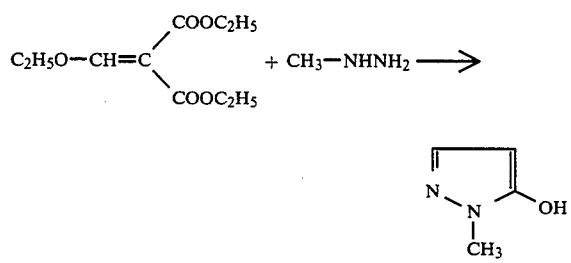

To a mixture of 150 ml of ethanol and 108 g (0.5 mol) of ethoxymethylenemalonate diethyl ester was added dropwise 23 g (0.5 mol) of methylhydrazine below 0° C. After completion of the reaction mixture was stirred for 1 hour at room temperature, and then refluxed for 1 hour. Then the reaction mixture was added to 200 ml of concentrated hydrochloric acid and refluxed for 2 hours. After completion of the reaction, the reflux condenser was replaced by a water separator and, after adding butanol, the reaction mixture was subjected to azeotropic dehydration. After completion of the dehydration, butanol in the mixture was distilled off under reduced pressure and the residue was recrystallized from isopropylalcohol to give 38 g (0.38 mol) of the title compound as a hydrochloric salt (yield: 76%), m.p.: 135°–147° C.

SYNTHESIS EXAMPLE 2

Synthesis of 4-(2,4-dichloro-3-methylbenzoyl)-1-methyl)-1-methyl-5-hydroxypyrazole (Compound No. 3)

In a 20% aqueous solution of 11.2 g (0.2 mol) of potassium hydroxide was dissolved 13.5 g (0.1 mol) of 1-methyl-5-hydroxylpyrazole hydrochloride and then 50 ml of chloroform was added to the resulting solution to give a two-layered mixture. Then, 22.4 g (0.1 mol) of 2,4-dichloro-3-methylbenzoyl chloride was added dropwise to the mixture and the resulting reaction system was subjected to reaction for 2 hours at room temperature. Chloroform layer was separated from the reaction liquid and dried. Then the solvent was distilled off under reduced pressure. The resulting solid was incorporated with 25 ml of 1,4-dioxane and 27.6 g (0.2 mol)

of potassium carbonate and then heated at 100° to 120° C. Solid matter was obtained by the reaction approximately for 1 hour. After solvent was distilled off, the solid was added with 30 ml of isopropylalcohol and then refluxed for 30 minutes. The resulting powdery solid was poured into ice-water to dissolve the solid therein and acidified with hydrochloric acid. The solid thus produced was filtered off, dried and recrystallized from 95% ethanol to give 20.2 g of the end product (yield 71%), m.p. 131.0°~135.0° C.

$^1$H-NMR(CDCl$_3$, δ, ppm): 2.50(3H, S), 3.66(3H, S), 7.10~7.46(3H), 8.16(1H, S).

SYNTHESIS EXAMPLE 3

Synthesis of 4-(2,4-dichlorobenzoyl)-1-methyl-5-benzoyloxypyrazole (Compound No. 11)

4-(2,4-dichlorobenzoyl)-1-methyl-5-hydroxylpyrazole 2.71 g (0.01 mol) was dissolved in a solution of 1.01 g (0.01 mol) of triethylamine in 30 ml of absolute benzene. Then a solution of 1.41 g (0.01 mol) of benzoylchloride in 5 ml of absolute benzene was added dropwise thereto under stirring at room temperature and then the resulting mixture was heated at 40° to 50° C. for 30 minutes. After cooling the reaction mixture, the resulting salt was filtered off and benzene was distilled off therefrom under reduced pressure. The resulting oil was purified by column chromatography on silica gel eluting with benzene to give 3.26 g of the end product (yield 87%), m.p. 119°~120° C.

$^1$H-NMR(δ, ppm, CDCl$_3$): 3.72(3H, S), 7.16~8.04(9H).

SYNTHESIS EXAMPLE 4

Synthesis of 4-(2,4-dichloro-3-methylbenzoyl)-1-methyl-5-(4-methylbenzenesulfonyloxy)pyrazole (Compound No. 19)

To a solution of 1.43 g (0.005 mol) of 4-(2,4-dichloro-3-methylbenzoyl)-1-methyl-5-hydroxypyrazole and 0.51 g (0.005 mol) of triethylamine in 20 ml of absolute benzene was added 0.95 g of p-toluenesulfonyl chloride and the resulting mixture was stirred for one hour at room temperature. The salt thus produced was filtered off and subjected to after-treatment and purification similarly as in Synthesis Example 3 to give 2.0 g of the final product (yield 91%).

$^1$H-NMR(δ, ppm, CDCl$_3$): 2.40(3H, S), 2.43(3H, S), 3.77(3H, S), 6.89~7.87(7H).

SYNTHESIS EXAMPLE 5

Synthesis of 4-(2,3,4-trichlorobenzoyl)-1-methyl-5-methanesulfonyloxypyrazole (Compound No. 20)

To a solution of 1.53 g (0.005 mol) of 4-(2,3,4-trichlorobenzoyl)-1-methyl-5-hydroxypyrazole and 0.51 g (0.005 mol) of triethylamine in 20 ml of absolute benzene was added dropwise 0.57 g (0.005 mol) of methanesulfonyl chloride with stirring. The same reaction and after-treatment as in Synthesis Example 4 were repeated to give 1.7 g of the final product (yield 89%), m.p. 152°-155° C.

$^1$H-NMR(δ, ppm, CDCl$_3$): 3.59(3H, S), 3.89(3H, S), 7.15~7.58(3H).

SYNTHESIS EXAMPLE 6

Synthesis of O,O-diethyl-O-[4-(2,4-dichlorobenzoyl)-1-methyl-5-pyrazolyl]phosphorothionate (Compound No. 13)

In 20 ml of benzene were dissolved 1.36 g (0.005 mol) of 4-(2,4-dichlorobenzoyl)-1-methyl-5-hydroxypyrazole, 0.51 g (0.005 mol) of triethylamine and 0.94 g (0.005 mol) of diethyl chlorothiophosphate, and the resulting solution was heated under reflux with stirring for 5 hours. After completion of the reaction, the reaction system was subjected to the same after-treatment and purification as in Synthesis Example 3 to give 0.53 g of the final product as an oil (yield 25%).

$^1$H-NMR(δ, ppm, CDCl$_3$): 1.35(6H, t, J=7 Hz), 3.82(3H, S), 4.28(4H, q, d, J=7 Hz, J=10 Hz), 7.39~7.50(4H).

SYNTHESIS EXAMPLE 7

Synthesis of 4-(2-chloro-4-methanesulfonylbenzoyl)-1-methyl-5-hydroxypyrazole 2-chloro-4-methanesulfonyl benzoic acid 3.87 g (0.0165 mol) was added to 40 ml of tert.-butanol, and then were added thereto 3.47 g (0.0168 mol) of N,N'-dicyclohexylcarbodiimide and 1.21 g (0.088 mol) of anhydrous potassium carbonate. The resulting mixture was incorporated with 1.65 g (0.0168 mol) of 1-methyl-5-hydroxypyrazole with stirring at room temperature and heated at 60° C. to effect reaction for 5 hours. After completion of the reaction, solvent was distilled away from the reaction mixture under reduced pressure and the resulting residue was washed with chloroform. Thereafter, the residue was incorporated with 30 ml of water and stirred. Insoluble matter was filtered out. The aqueous solution thus obtained was incorporated with conc. hydrochloric acid to adjust the pH thereof to 1 or lower and then with chloroform to effect extraction. An organic layer was separated, dried over anhydrous sodium sulfate, freed of solvent by distillation under reduced pressure, and dried to give 2.75 g of the final product (yield: 53%), m.p. 272°-275° C.

SYNTHESIS EXAMPLE 8

Synthesis of 4-(2-chloro-4-methanesulfonylbenzoyl)-1-methyl-5-(4-methylbenzenesulfonyloxy)-pyrazole To 30 ml of benzene were added 1.57 g (0.005 mol) of 4-(2-chloro-4-methanesulfonylbenzoyl)-1-methyl-5-hydroxypyrazole 1.57 g (0.005 mol) and 0.51 g (0.005 mol) of triethylamine to give a homogeneous solution. Then was added thereto 0.95 g (0.005 mol) of p-toluenesulfonyl chloride and the resulting mixture was subjected to reaction at the reflux temperature of the solvent for 3 hours.

After completion of the reaction, the reaction mixture was allowed to cool and added with water to separate liuids. Benzene layer was washed successively with 5% aqueous solution of sodium hydrogencarbonate, water and saturated brine and dried over anhydrous sodium sulfate. The solvent was distilled off under reduced pressure and the resulting residue was purified through silica gel chromatography eluting with benzene/ethyl acetate to give 1.76 g of the final product (yield 75%), m.p. 141.0°~145.0° C.

In the similar manner as in Synthesis Examples 1 through 8 the compounds listed in Table 1 were synthesized. The compounds obtained in Synthesis Examples 2 through 8 are also listed in Table 1.

TABLE 1

The compounds of the formula:

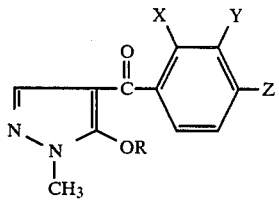

| Compound No. | X | Y | Z | R | Appearance or m.p. (°C.) | $^1$H—NMR (δ, ppm, CDCl$_3$) N—C$\underline{H}_3$ | Other characteristic peaks |
|---|---|---|---|---|---|---|---|
| 1 | Cl | H | Cl | H | 181.0~181.5 | 3.68 | 7.38~7.61(4H), 8.01(1H, S) |
| 2 | NO$_2$ | H | Cl | H | 203.0~207.0 | 3.61 | 7.29(1H, S) |
| 3 | Cl | CH$_3$ | Cl | H | 131.0~135.0 | 3.66 | 2.50(3H, S), 7.32(1H, S) |
| 4 | Cl | H | SO$_2$CH$_3$ | H | 272.0~275.0 | 3.60 | 3.24(3H, S), 7.20(1H, S) |
| 5 | Br | H | Br | H | 170.0~174.0 | 3.64 | 7.30(1H, S) |
| 6 | Cl | Cl | Cl | H | 148.0~150.0 | 3.68 | 7.30(1H, S), 7.32(2H, double α) |
| 7 | Cl | Br | Cl | H | 168.0~170.0 | 3.68 | 7.33(1H, S) |
| 8 | Cl | H | F | H | 158.0~161.0 | 3.67 | 7.34(1H, S) |
| 9 | Cl | CH$_3$ | F | H | 122.0~124.0 | 3.62 | 2.32(3H, d, J=2Hz), 7.26(1H, S) |
| 10 | Cl | H | Cl | —COCH$_3$ | oil | 3.66 | 2.27(3H, S), 7.31~7.45(3H), 7.56(1H, S) |
| 11 | Cl | H | Cl | —CO—C$_6$H$_5$ | 119.0~120.0 | 3.72 | 7.16~8.04(9H) |
| 12 | Cl | H | Cl | —CON(CH$_3$)$_2$ | 160.0~162.0 | 3.69 | 2.94(6H, S), 7.29~7.44(3H), 7.64(1H, S) |
| 13 | Cl | H | Cl | P(S)(OC$_2$H$_5$)$_2$ | oil | 3.82 | 1.35(6H, t, J=7Hz), 4.28(4H, q, d, J=7Hz, J=10Hz) |
| 14 | Cl | H | Cl | SO$_2$CH$_3$ | 115.0~118.0 | 3.85 | 3.54(3H, S), 7.32~7.44(4H) |
| 15 | Cl | H | Cl | —CO-furyl | 109.0~112.0 | 3.70 | — |
| 16 | Cl | H | Cl | (nitro-phenoxy-dichlorophenyl carbonyl) | — | 3.85 | 6.91~8.23(10H) |
| 17 | Cl | H | Cl | (3-chlorobenzothiophene-2-carbonyl) | 177.0~179.0 | 3.78 | — |
| 18 | NO$_2$ | H | Cl | SO$_2$CH$_3$ | 105.0~108.0 | 3.88 | 3.54(3H, S) |
| 19 | Cl | CH$_3$ | Cl | SO$_2$-C$_6$H$_4$-CH$_3$ | oil | 3.77 | 2.40(3H, S), 2.43(3H, S) |

TABLE 1-continued

The compounds of the formula:

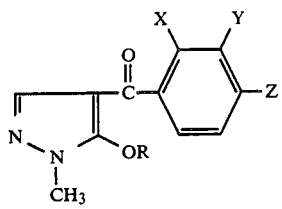

| Compound No. | X | Y | Z | R | Appearance or m.p. (°C.) | ¹H—NMR (δ, ppm, CDCl₃) N—C$\underline{H}_3$ | Other characteristic peaks |
|---|---|---|---|---|---|---|---|
| 20 | Cl | Cl | Cl | SO₂CH₃ | 152.0~155.0 | 3.89 | 3.59(3H, S) |
| 21 | Cl | Cl | Cl | SO₂—C₆H₄—CH₃ | oil | 3.74 | 2.40(3H, S) |
| 22 | Cl | Cl | Cl | —CO—C₆H₄(CH₃) | 172.0~175.0 | 3.76 | 2.60(3H, S) |
| 23 | Cl | CH₃ | F | SO₂—C₆H₄—CH₃ | oil | 3.77 | 2.28(3H, d, J=2Hz), 2.40(3H, S) |
| 24 | Cl | Br | Cl | SO₂CH₃ | oil | 3.80 | 3.26(3H, S), 7.29(2H, double d), 7.63(1H, S) |
| 25 | Cl | Cl | Cl | P(=S)(OC₂H₅)₂ | oil | 3.81 | 1.37(6H, t, J=7Hz), 4.28(4H, q, d, J=7Hz, J=10Hz), 7.33(2H, d, d), 7.43(1H, S) |
| 26 | Cl | Br | Cl | SO₂—C₆H₄—CH₃ | oil | 3.77 | 2.43(3H, S) |
| 27 | Br | H | Br | SO₂—C₆H₄—CH₃ | oil | 3.77 | 2.42(3H, S), 7.00~7.83(8H) |
| 60 | Cl | H | SO₂CH₃ | SO₂CH₃ | 148~151 | 3.87 | 3.09(3H, S), 3.56(3H, S) |
| 83 | Cl | H | SO₂CH₃ | SO₂—C₆H₄—CH₃ | 141~145 | 3.69 | 2.43(3H, S), 3.05(3H, S) |
| 324 | Cl | H | SO₂CH₃ | CH₂—C₆H₅ | 126~128 | 3.51 | 3.08(3H, S), 5.55(2H, S) |
| 298 | Cl | H | SO₂CH₃ | CH₂C≡CH | 157~158 | 3.73 | 2.54(1H, t), 3.07(3H, S), 5.23(2H, d) |
| 299 | Cl | H | SO₂CH₃ | CH₂CN | 166~167 | 3.77 | 3.08(3H, S), 5.43(2H, S) |

The compounds listed in Table 2 can be readily synthesized in accordance with the foregoing synthesis examples. Incidentally, it should be noted that the compounds according to the present invention are not restricted to these compounds.

TABLE 2

The compounds of the formula:

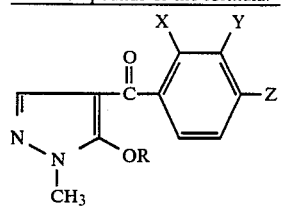

| Compound No. | X | Y | Z | R |
|---|---|---|---|---|
| 28 | Cl | H | Cl | COC$_2$H$_5$ |
| 29 | Cl | H | Cl | COCH(CH$_3$)$_2$ |
| 30 | Cl | H | Cl | COC(CH$_3$)$_3$ |
| 31 | Cl | H | Cl | SO$_2$CF$_3$ |
| 32 | Cl | H | Cl | SO$_2$N(CH$_3$)$_2$ |
| 33 | Cl | H | Cl | SO$_2$–C$_6$H$_5$ |
| 34 | Cl | H | Cl | SO$_2$–C$_6$H$_4$–Cl |
| 35 | Cl | H | Cl | SO$_2$–C$_6$H$_4$–CH$_3$ |
| 36 | Cl | H | Cl | P(O)(OCH$_3$)$_2$ |
| 37 | Cl | H | Cl | P(O)(OC$_2$H$_5$)$_2$ |
| 38 | Cl | H | Cl | SO$_2$–C$_6$H$_3$Cl$_2$ |
| 39 | Cl | H | Cl | COOC$_2$H$_5$ |
| 40 | Cl | H | Cl | CSCH$_2$–C$_6$H$_5$ |
| 41 | Cl | H | Cl | CO–C$_6$H$_{11}$ |
| 42 | Cl | H | Cl | COCH$_2$O–C$_6$H$_3$Cl$_2$ |
| 43 | Cl | H | Cl | COCH$_2$–C$_6$H$_5$ |
| 44 | Cl | H | Cl | COCH=CH–C$_6$H$_5$ |
| 45 | Cl | H | Cl | COCH$_2$Cl |
| 46 | Cl | H | Cl | COCH$_2$NH–C$_6$H$_5$ |
| 47 | Cl | H | Cl | COCH$_2$CH=CH$_2$ |
| 48 | Cl | H | Cl | COCCl=CCl$_2$ |
| 49 | Cl | H | Cl | COCH=CH$_2$ |
| 50 | Cl | H | Cl | COCH$_2$CH(CH$_3$)$_2$ |
| 51 | Cl | H | Cl | COCH=CH–C$_6$H$_4$–Cl |
| 52 | Cl | H | Cl | COCH$_2$NH–C$_6$H$_3$Cl$_2$ |
| 53 | Cl | H | Cl | COCH$_2$–C$_6$H$_4$–CH$_3$ |
| 54 | Cl | H | Cl | COOC(CH$_3$)$_3$ |
| 55 | Cl | H | Cl | COOCH$_2$–C$_6$H$_5$ |
| 56 | Cl | H | Cl | COCH$_2$O–C$_6$H$_5$ |
| 57 | Cl | H | SO$_2$CH$_3$ | COCH$_3$ |

TABLE 2-continued

The compounds of the formula:

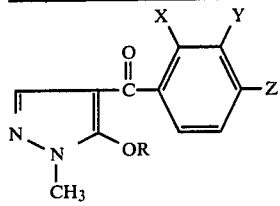

| Compound No. | X | Y | Z | R |
|---|---|---|---|---|
| 58 | Cl | H | SO₂CH₃ | COC₂H₅ |
| 59 | Cl | H | SO₂CH₃ | COC(CH₃)₃ |
| 61 | Cl | H | SO₂CH₃ | SO₂CF₃ |
| 62 | Cl | H | SO₂CH₃ | SO₂—C₆H₅ |
| 63 | Cl | H | SO₂CH₃ | SO₂—C₆H₄Cl |
| 64 | Cl | H | SO₂CH₃ | P(=S)(OC₂H₅)₂ |
| 65 | Cl | H | SO₂CH₃ | P(=O)(OCH₃)₂ |
| 66 | Cl | H | SO₂CH₃ | P(=O)(OC₂H₅)₂ |
| 67 | Cl | H | SO₂CH₃ | CON(CH₃)₂ |
| 68 | Cl | H | SO₂CH₃ | COOC₂H₅ |
| 69 | Cl | H | SO₂CH₃ | C(=S)CH₂—C₆H₅ |
| 70 | Cl | H | SO₂CH₃ | COCH₂O—C₆H₅ |
| 71 | Cl | H | SO₂CH₃ | COCH₂O—C₆H₃Cl₂ |
| 72 | Cl | H | SO₂CH₃ | COCH=CH—C₆H₁₁ |
| 73 | Cl | H | SO₂CH₃ | COCH₂—C₆H₅ |
| 74 | Cl | H | SO₂CH₃ | COCH₂Cl |

TABLE 2-continued

The compounds of the formula:

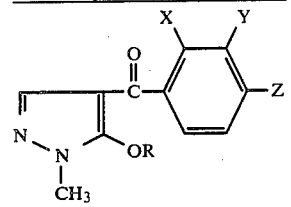

| Compound No. | X | Y | Z | R |
|---|---|---|---|---|
| 75 | Cl | H | SO₂CH₃ | COCH₂NH—C₆H₅ |
| 76 | Cl | H | SO₂CH₃ | COCH₂NH—C₆H₄Cl |
| 77 | Cl | H | SO₂CH₃ | COCCl=CCl₂ |
| 78 | Cl | H | SO₂CH₃ | COOC(CH₃)₃ |
| 79 | Cl | H | SO₂CH₃ | CO-furyl |
| 80 | Cl | H | SO₂CH₃ | SO₂N(CH₃)₂ |
| 81 | Cl | H | SO₂CH₃ | CO—C₆H₅ |
| 82 | Cl | H | SO₂CH₃ | CO—C₆H₃Cl₂ |
| 84 | NO₂ | H | Cl | COCH₃ |
| 85 | NO₂ | H | Cl | COC₂H₅ |
| 86 | NO₂ | H | Cl | COC(CH₃)₃ |
| 87 | NO₂ | H | Cl | COOCH₂—C₆H₅ |
| 88 | NO₂ | H | Cl | SO₂CF₃ |
| 89 | NO₂ | H | Cl | SO₂—C₆H₅ |
| 90 | NO₂ | H | Cl | SO₂—C₆H₄Cl |
| 91 | NO₂ | H | Cl | P(=S)(OC₂H₅)₂ |

TABLE 2-continued

The compounds of the formula:

(structure shown: pyrazole with N-CH3, OR group, connected via C=O to phenyl ring bearing X, Y, Z substituents)

| Compound No. | X | Y | Z | R |
|---|---|---|---|---|
| 92 | NO₂ | H | Cl | P(OCH₃)₂ (=O) |
| 93 | NO₂ | H | Cl | P(OC₂H₅)₂ (=O) |
| 94 | NO₂ | H | Cl | C(=O)N(CH₃)₂ |
| 95 | NO₂ | H | Cl | COOC₂H₅ |
| 96 | NO₂ | H | Cl | C(=S)CH₂-phenyl |
| 97 | NO₂ | H | Cl | C(=O)CH₂O-phenyl |
| 98 | NO₂ | H | Cl | C(=O)CH₂O-(2,4-dichlorophenyl) |
| 99 | NO₂ | H | Cl | C(=O)CH=CH-phenyl |
| 100 | NO₂ | H | Cl | C(=O)CH₂-phenyl |
| 101 | NO₂ | H | Cl | C(=O)CH₂Cl |
| 102 | NO₂ | H | Cl | C(=O)CH₂NH-phenyl |
| 103 | NO₂ | H | Cl | C(=O)CH₂NH-(4-chlorophenyl) |
| 104 | NO₂ | H | Cl | C(=O)CCl=CCl₂ |
| 105 | NO₂ | H | Cl | COOC(CH₃)₃ |
| 106 | NO₂ | H | Cl | C(=O)-furyl |
| 107 | NO₂ | H | Cl | SO₂N(CH₃)₂ |
| 108 | NO₂ | H | Cl | C(=O)-phenyl |
| 109 | NO₂ | H | Cl | C(=O)-(2,4-dichlorophenyl) |
| 110 | Br | H | Br | COCH₃ |
| 111 | Br | H | Br | COC₂H₅ |
| 112 | Br | H | Br | COC(CH₃)₃ |
| 113 | Br | H | Br | SO₂CH₃ |
| 114 | Br | H | Br | SO₂CF₃ |
| 115 | Br | H | Br | SO₂-phenyl |
| 116 | Br | H | Br | SO₂-(chlorophenyl) |
| 117 | Br | H | Br | P(OC₂H₅)₂ (=S) |
| 118 | Br | H | Br | P(OCH₃)₂ (=O) |
| 119 | Br | H | Br | P(OC₂H₅)₂ (=O) |
| 120 | Br | H | Br | C(=O)N(CH₃)₂ |
| 121 | Br | H | Br | COOC₂H₅ |
| 122 | Br | H | Br | C(=S)CH₂-phenyl |
| 123 | Br | H | Br | C(=O)CH₂O-phenyl |

TABLE 2-continued

The compounds of the formula:

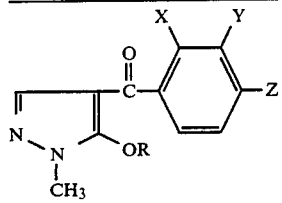

| Compound No. | X | Y | Z | R |
|---|---|---|---|---|
| 124 | Br | H | Br | ![](CCH2O-C6H4-Cl, C=O) |
| 125 | Br | H | Br | CCH=CH-C6H5, C=O |
| 126 | Br | H | Br | CCH2-C6H5, C=O |
| 127 | Br | H | Br | CCH2Cl, C=O |
| 128 | Br | H | Br | CCH2NH-C6H5, C=O |
| 129 | Br | H | Br | CCH2NH-C6H4-Cl, C=O |
| 130 | Br | H | Br | CCCl=CCl2, C=O |
| 131 | Br | H | Br | COOC(CH3)3 |
| 132 | Br | H | Br | C(=O)-furan |
| 133 | Br | H | Br | SO2N(CH3)2 |
| 134 | Br | H | Br | C(=O)-C6H5 |
| 135 | Br | H | Br | C(=O)-C6H3Cl2 |
| 136 | Cl | H | F | COCH3 |
| 137 | Cl | H | F | COC2H5 |
| 138 | Cl | H | F | COC(CH3)3 |
| 139 | Cl | H | F | SO2CH3 |
| 140 | Cl | H | F | SO2CF3 |

TABLE 2-continued

The compounds of the formula:

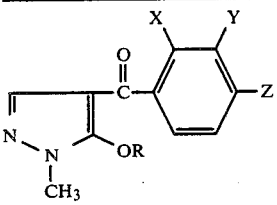

| Compound No. | X | Y | Z | R |
|---|---|---|---|---|
| 141 | Cl | H | F | SO2-C6H5 |
| 142 | Cl | H | F | SO2-C6H4-Cl |
| 143 | Cl | H | F | P(=S)(OC2H5)2 |
| 144 | Cl | H | F | P(=O)(OCH3)2 |
| 145 | Cl | H | F | P(=O)(OC2H5)2 |
| 146 | Cl | H | F | CN(CH3)2, C=O |
| 147 | Cl | H | F | COOC2H5 |
| 148 | Cl | H | F | CCH2-C6H5, C=S |
| 149 | Cl | H | F | CCH2O-C6H5, C=O |
| 150 | Cl | H | F | CCH2O-C6H3Cl2, C=O |
| 151 | Cl | H | F | CCH=CH-C6H5, C=O |
| 152 | Cl | H | F | CCH2-C6H5, C=O |
| 153 | Cl | H | F | CCH2Cl, C=O |

TABLE 2-continued

The compounds of the formula:

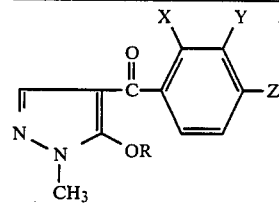

| Compound No. | X | Y | Z | R |
|---|---|---|---|---|
| 154 | Cl | H | F | -C(=O)CH₂NH-C₆H₅ |
| 155 | Cl | H | F | -C(=O)CH₂NH-C₆H₄Cl |
| 156 | Cl | H | F | -C(=O)CCl=CCl₂ |
| 157 | Cl | H | F | COOC(CH₃)₃ |
| 158 | Cl | H | F | -C(=O)-(2-furyl) |
| 159 | Cl | H | F | SO₂N(CH₃)₂ |
| 160 | Cl | H | F | -C(=O)-C₆H₅ |
| 161 | Cl | H | F | -C(=O)-C₆H₃Cl₂ |
| 162 | Cl | CH₃ | F | COCH₃ |
| 163 | Cl | CH₃ | F | COC₂H₅ |
| 164 | Cl | CH₃ | F | COC(CH₃)₃ |
| 165 | Cl | CH₃ | F | SO₂CH₃ |
| 166 | Cl | CH₃ | F | SO₂CF₃ |
| 167 | Cl | CH₃ | F | SO₂-C₆H₅ |
| 168 | Cl | CH₃ | F | SO₂-C₆H₄Cl |
| 169 | Cl | CH₃ | F | P(=S)(OC₂H₅)₂ |
| 170 | Cl | CH₃ | F | P(=O)(OCH₃)₂ |
| 171 | Cl | CH₃ | F | P(=O)(OC₂H₅)₂ |

TABLE 2-continued

The compounds of the formula:

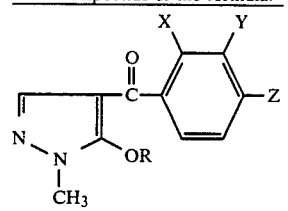

| Compound No. | X | Y | Z | R |
|---|---|---|---|---|
| 172 | Cl | CH₃ | F | CN(CH₃)₂ with =O |
| 173 | Cl | CH₃ | F | COOC₂H₅ |
| 174 | Cl | CH₃ | F | -C(=S)CH₂-C₆H₅ |
| 175 | Cl | CH₃ | F | -C(=O)CH₂O-C₆H₅ |
| 176 | Cl | CH₃ | F | -C(=O)CH₂O-C₆H₃Cl₂ |
| 177 | Cl | CH₃ | F | -C(=O)CH=CH-C₆H₅ |
| 178 | Cl | CH₃ | F | -C(=O)CH₂-C₆H₅ |
| 179 | Cl | CH₃ | F | -C(=O)CH₂Cl |
| 180 | Cl | CH₃ | F | -C(=O)CH₂NH-C₆H₅ |
| 181 | Cl | CH₃ | F | -C(=O)CH₂NH-C₆H₄Cl |
| 182 | Cl | CH₃ | F | -C(=O)CCl=CCl₂ |
| 183 | Cl | CH₃ | F | COOC(CH₃)₃ |
| 184 | Cl | CH₃ | F | -C(=O)-(2-furyl) |
| 185 | Cl | CH₃ | F | SO₂N(CH₃)₂ |

TABLE 2-continued

The compounds of the formula:

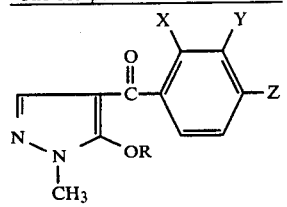

| Compound No. | X | Y | Z | R |
|---|---|---|---|---|
| 186 | Cl | CH₃ | F | —C(=O)—C₆H₅ |
| 187 | Cl | CH₃ | F | —C(=O)—C₆H₃Cl₂ (2,4-dichlorophenyl) |
| 188 | Cl | CH₃ | Cl | COCH₃ |
| 189 | Cl | CH₃ | Cl | COC₂H₅ |
| 190 | Cl | CH₃ | Cl | COC(CH₃)₃ |
| 191 | Cl | CH₃ | Cl | SO₂CH₃ |
| 192 | Cl | CH₃ | Cl | SO₂CF₃ |
| 193 | Cl | CH₃ | Cl | —SO₂—C₆H₅ |
| 194 | Cl | CH₃ | Cl | —SO₂—C₆H₄Cl |
| 195 | Cl | CH₃ | Cl | P(=S)(OC₂H₅)₂ |
| 196 | Cl | CH₃ | Cl | P(=O)(OCH₃)₂ |
| 197 | Cl | CH₃ | Cl | P(=O)(OC₂H₅)₂ |
| 198 | Cl | CH₃ | Cl | C(=O)N(CH₃)₂ |
| 199 | Cl | CH₃ | Cl | COOC₂H₅ |
| 200 | Cl | CH₃ | Cl | —C(=S)CH₂—C₆H₅ |
| 201 | Cl | CH₃ | Cl | —C(=O)CH₂O—C₆H₅ |
| 202 | Cl | CH₃ | Cl | —C(=O)CH₂O—C₆H₃Cl₂ (2,4-dichlorophenoxy) |
| 203 | Cl | CH₃ | Cl | —C(=O)CH=CH—C₆H₅ |
| 204 | Cl | CH₃ | Cl | —C(=O)CH₂—C₆H₅ |
| 205 | Cl | CH₃ | Cl | —C(=O)CH₂Cl |
| 206 | Cl | CH₃ | Cl | —C(=O)CH₂NH—C₆H₅ |
| 207 | Cl | CH₃ | Cl | —C(=O)CH₂NH—C₆H₄Cl |
| 208 | Cl | CH₃ | Cl | —C(=O)CCl=CCl₂ |
| 209 | Cl | CH₃ | Cl | COOC(CH₃)₃ |
| 210 | Cl | CH₃ | Cl | —C(=O)-furyl |
| 211 | Cl | CH₃ | Cl | SO₂N(CH₃)₂ |
| 212 | Cl | CH₃ | Cl | —C(=O)—C₆H₅ |
| 213 | Cl | CH₃ | Cl | —C(=O)—C₆H₃Cl₂ (2,4-dichlorophenyl) |
| 214 | Cl | Cl | Cl | COCH₃ |
| 215 | Cl | Cl | Cl | COC₂H₅ |
| 216 | Cl | Cl | Cl | COC(CH₃)₃ |
| 217 | Cl | Cl | Cl | SO₂CF₃ |
| 218 | Cl | Cl | Cl | —SO₂—C₆H₅ |

TABLE 2-continued

The compounds of the formula:

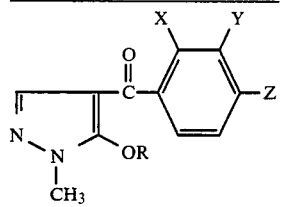

| Compound No. | X | Y | Z | R |
|---|---|---|---|---|
| 219 | Cl | Cl | Cl | SO₂–C₆H₄–Cl |
| 220 | Cl | Cl | Cl | $\overset{O}{\underset{\|}{P}}(OCH_3)_2$ |
| 221 | Cl | Cl | Cl | $\overset{O}{\underset{\|}{P}}(OC_2H_5)_2$ |
| 222 | Cl | Cl | Cl | $\overset{O}{\underset{\|}{C}}N(CH_3)_2$ |
| 223 | Cl | Cl | Cl | COOC₂H₅ |
| 224 | Cl | Cl | Cl | $\overset{S}{\underset{\|}{C}}CH_2$–C₆H₅ |
| 225 | Cl | Cl | Cl | $\overset{O}{\underset{\|}{C}}CH_2O$–C₆H₅ |
| 226 | Cl | Cl | Cl | $\overset{O}{\underset{\|}{C}}CH_2O$–C₆H₃Cl₂ |
| 227 | Cl | Cl | Cl | $\overset{O}{\underset{\|}{C}}CH=CH$–C₆H₅ |
| 228 | Cl | Cl | Cl | $\overset{O}{\underset{\|}{C}}CH_2$–C₆H₅ |
| 229 | Cl | Cl | Cl | $\overset{O}{\underset{\|}{C}}CH_2Cl$ |
| 230 | Cl | Cl | Cl | $\overset{O}{\underset{\|}{C}}CH_2NH$–C₆H₅ |
| 231 | Cl | Cl | Cl | $\overset{O}{\underset{\|}{C}}CH_2NH$–C₆H₄Cl |

TABLE 2-continued

The compounds of the formula:

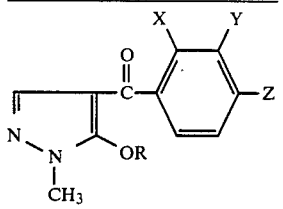

| Compound No. | X | Y | Z | R |
|---|---|---|---|---|
| 232 | Cl | Cl | Cl | $\overset{O}{\underset{\|}{C}}CCl=CCl_2$ |
| 233 | Cl | Cl | Cl | COOC(CH₃)₃ |
| 234 | Cl | Cl | Cl | furan-2-carbonyl |
| 235 | Cl | Cl | Cl | SO₂N(CH₃)₂ |
| 236 | Cl | Cl | Cl | $\overset{O}{\underset{\|}{C}}$–C₆H₅ |
| 237 | Cl | Cl | Cl | $\overset{O}{\underset{\|}{C}}$–C₆H₃Cl₂ |
| 238 | Cl | Cl | Cl | $\overset{O}{\underset{\|}{C}}CH_2N(CH_3)_2$ |
| 239 | Cl | Br | Cl | COCH₃ |
| 240 | Cl | Br | Cl | COC₂H₅ |
| 241 | Cl | Br | Cl | COC(CH₃)₃ |
| 242 | Cl | Br | Cl | SO₂CF₃ |
| 243 | Cl | Br | Cl | SO₂–C₆H₅ |
| 244 | Cl | Br | Cl | SO₂–C₆H₄Cl |
| 245 | Cl | Br | Cl | $\overset{S}{\underset{\|}{P}}(OC_2H_5)_2$ |
| 246 | Cl | Br | Cl | $\overset{O}{\underset{\|}{P}}(OCH_3)_2$ |
| 247 | Cl | Br | Cl | $\overset{O}{\underset{\|}{P}}(OC_2H_5)_2$ |
| 248 | Cl | Br | Cl | $\overset{O}{\underset{\|}{C}}N(CH_3)_2$ |
| 249 | Cl | Br | Cl | COOC₂H₅ |

TABLE 2-continued

The compounds of the formula:

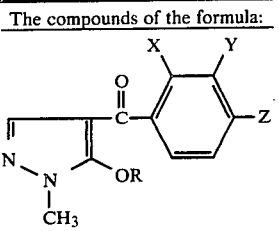

| Compound No. | X | Y | Z | R |
|---|---|---|---|---|
| 250 | Cl | Br | Cl | CCH₂—phenyl, C=S |
| 251 | Cl | Br | Cl | CCH₂O—phenyl, C=O |
| 252 | Cl | Br | Cl | CCH₂O—(2,4-dichlorophenyl), C=O |
| 253 | Cl | Br | Cl | CCH=CH—phenyl, C=O |
| 254 | Cl | Br | Cl | CCH₂—phenyl, C=O |
| 255 | Cl | Br | Cl | CCH₂Cl, C=O |
| 256 | Cl | Br | Cl | CCH₂NH—phenyl, C=O |
| 257 | Cl | Br | Cl | CCH₂NH—(4-chlorophenyl), C=O |
| 258 | Cl | Br | Cl | CCCl=CCl₂, C=O |
| 259 | Cl | Br | Cl | COOC(CH₃)₃ |
| 260 | Cl | Br | Cl | C(=O)—furyl |
| 261 | Cl | Br | Cl | SO₂N(CH₃)₂ |
| 262 | Cl | Br | Cl | C(=O)—phenyl |

TABLE 2-continued

The compounds of the formula:

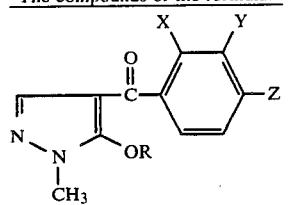

| Compound No. | X | Y | Z | R |
|---|---|---|---|---|
| 263 | Cl | Br | Cl | C(=O)—(2,4-dichlorophenyl) |
| 264 | NO₂ | H | SO₂CH₃ | COCH₃ |
| 265 | NO₂ | H | SO₂CH₃ | SO₂CH₃ |
| 266 | NO₂ | H | SO₂CH₃ | SO₂CF₃ |
| 267 | NO₂ | H | SO₃CH₃ | SO₂—phenyl |
| 268 | NO₂ | H | SO₃CH₃ | SO₂—(4-chlorophenyl) |
| 269 | NO₂ | H | SO₂CH₃ | SO₂—(4-methylphenyl) |
| 270 | NO₂ | H | SO₂CH₃ | CH₂—phenyl |
| 271 | NO₂ | H | SO₂CH₃ | H |
| 272 | SO₂CH₃ | H | Cl | SO₃CH₃ |
| 273 | SO₂CH₃ | H | Cl | SO₂—phenyl |
| 274 | SO₂CH₃ | H | Cl | SO₂—(4-methylphenyl) |
| 275 | SO₂CH₃ | H | Cl | CO—phenyl |
| 276 | SO₂CH₃ | H | Cl | CH₂—phenyl |
| 277 | SO₂CH₃ | H | Cl | H |
| 278 | SO₂CH₃ | H | Cl | COCH₃ |
| 279 | SO₂CH₃ | H | SO₂CH₃ | COCH₃ |
| 280 | SO₂CH₃ | H | SO₂CH₃ | SO₂CH₃ |

TABLE 2-continued

The compounds of the formula:

$$\text{structure with X, Y, Z, OR substituents on pyrazole-benzoyl}$$

| Compound No. | X | Y | Z | R |
|---|---|---|---|---|
| 281 | SO₂CH₃ | H | SO₂CH₃ | -SO₂-C₆H₅ |
| 282 | SO₂CH₃ | H | SO₂CH₃ | -SO₂-C₆H₄-CH₃ |
| 283 | SO₂CH₃ | H | SO₂CH₃ | -CO-C₆H₅ |
| 284 | SO₂CH₃ | H | SO₂CH₃ | H |
| 285 | Cl | H | SO₂CH₃ | COC₂H₅ |
| 286 | Cl | H | SO₂CH₃ | SO₂CF₃ |
| 287 | Cl | H | SO₂CH₃ | COCH₃ |
| 288 | Cl | H | SO₂CH₃ | -SO₂-C₆H₅ |
| 289 | Cl | H | SO₂CH₃ | -SO₂-C₆H₄-Cl |
| 290 | Cl | H | SO₂CH₃ | CH₃ |
| 291 | Cl | H | SO₂CH₃ | C₂H₅ |
| 292 | Cl | H | SO₂CH₃ | CH₂CH₂CH₃ |
| 293 | Cl | H | SO₂CH₃ | CH(CH₃)₂ |
| 294 | Cl | H | SO₂CH₃ | CH₂CH₂CH₂CH₃ |
| 295 | Cl | H | SO₂CH₃ | CH₂CH=CH₂ |
| 296 | Cl | H | SO₂CH₃ | CH₂CCl=CH₂ |
| 297 | Cl | H | SO₂CH₃ | -C₆H₁₁ (cyclohexyl) |
| 298 | Cl | H | SO₂CH₃ | CH₂C≡CH |
| 299 | Cl | H | SO₂CH₃ | CH₂CN |
| 300 | Cl | H | SO₂CH₃ | CH₂COOC₂H₅ |
| 301 | Cl | H | SO₂CH₃ | CH₂CH=CHCOOC₂H₅ |
| 302 | Cl | H | SO₂CH₃ | CH₂CH₂OH |
| 303 | Cl | H | SO₂CH₃ | CH₂CH=CHCOOCH₃ |
| 304 | Cl | H | SO₂CH₃ | CH₂CH=CHCH₂Cl |
| 305 | Cl | H | SO₂CH₃ | CH₂CH=CHCH₃ |
| 306 | Cl | H | SO₃CH₃ | CH₂CBr=CH₂ |
| 307 | Cl | H | SO₂CH₃ | CH₂C≡CCH₃ |
| 308 | Cl | H | SO₂CH₃ | CH₂CH₂Cl |
| 309 | Cl | H | SO₂CH₃ | -C₆H₄-NO₂ |
| 310 | Cl | H | SO₂CH₃ | -C₆H₄-Cl (o-Cl) |
| 311 | Cl | H | SO₂CH₃ | -C₆H₃-Cl₂ |
| 312 | Cl | H | SO₂CH₃ | -C₆H₄-CH₃ (p) |
| 313 | Cl | H | SO₂CH₃ | -C₆H₄-CH₃ (o) |
| 314 | Cl | H | SO₂CH₃ | -C₆H₄-Br (p) |
| 315 | NO₂ | H | SO₂CH₃ | CH₃ |
| 316 | NO₂ | H | SO₂CH₃ | CH₂CH=CH₂ |
| 317 | NO₂ | H | SO₂CH₃ | CH₂CN |
| 318 | NO₂ | H | SO₂CH₃ | CH₂C≡CH |
| 319 | SO₂CH₃ | H | SO₂CH₃ | CH₃ |
| 320 | SO₂CH₃ | H | SO₂CH₃ | CH₂CH=CH₂ |
| 321 | SO₂CH₃ | H | SO₂CH₃ | CH₂C≡CH |
| 322 | SO₂CH₃ | H | SO₂CH₃ | CH₂CN |
| 323 | Cl | H | SO₂CH₃ | COCCl=CCl₂ |

When the compounds according to the present invention are used for a herbicide, they may be applied generally together with appropriate carriers such as solid carriers, e.g. clay, talc, bentonite, diatomaceous earth, etc; or liquid carriers, e.g. water, alcohols (methanol, ethanol, etc.), aromatic hydrocarbons (benzene, toluene, xylene, etc.), chlorinated hydrocarbons, ethers, ketones, esters (ethyl acetate, etc.), acid amides (dimethylformamide, etc.). It is possible to add, as necessary, surfactants, dispersing agents, suspending agents, penetrating agents, spreaders, stabilizers, etc. to form arbitrary formulations such as emulsifiable concentrate, wettable powder, flowable (Suspension Concentrate), granule etc. for practical use.

If necessary, the compounds according to the invention may be mixed, during formulation or application, with other herbicides, various insecticides, bacteriocides, plant growth-regulator, cooperants, etc.

The other herbicides include the compounds described in "Farm Chemicals Handbook" 69th year of publication (1983).

In the following formulation examples, parts are by weight unless otherwise specified.

| Formulation Example 1: Emulsifiable concentrate | |
|---|---|
| Compound No. 10 of the invention | 30 parts |
| xylene | 45 parts |
| Sorpol 2680 (a mixture of non-ionic surfactant and anionic surfactant; trade name supplied by Toho Chemical Co., Ltd., Japan) | 10 parts |
| dimethylformamide | 15 parts |

The above ingredients are homogeneously blended with one another to give an emulsifiable concentrate. When in use, it is diluted with a suitable amount of water and applied.

| Formulation Example 2: Emulsifiable concentrate | |
|---|---|
| Compound No. 4 of the invention | 20 parts |
| xylene | 75 parts |
| Sorpol 2680 (a mixture of non-ionic surfactant and anionic surfactant; trade name supplied by Toho Chemical Co., Ltd., Japan) | 5 parts |

The above ingredients are homogeneously blended with one another to give an emulsifiable concentrate. When in use, it is diluted with a suitable amount of water and applied.

| Formulation Example 3: Wettable powder | |
|---|---|
| Compound No. 11 of the invention | 50 parts |
| Zeeklite A (kaolin type clay: trade name supplied by Ziecleid Industries Co., Ltd., Japan) | 46 parts |
| Sorpol 5039 (a mixture of non-ionic surfactant and anionic surfactant: trade name supplied by Toho Chemical Co., Ltd., Japan) | 2 parts |
| Carplex (coagulation inhibitor) (white carbon: trade name supplied by Shionogi Pharmaceutical Co., Ltd., Japan) | 2 parts |

The above ingredients are homogeneously crushed and mixed to give wettable powder. When in use, this wettable powder is diluted with an appropriate amount of water and applied.

| Formulation Example 4: Wettable powder | |
|---|---|
| Compound No. 4 of the invention | 50 parts |
| Zeeklite A (kaolin type clay: trade name supplied by Ziecleid Industries Co., Ltd., Japan) | 46 parts |
| Sorpol 5039 (a mixture of non-ionic surfactant and anionic surfactant: trade name supplied by Toho Chemical Co., Ltd., Japan) | 2 parts |
| Carplex (coagulation inhibitor) (white carbon: trade name supplied by Shionogi Pharmaceutical Co., Ltd., Japan) | 2 parts |

The above ingredients are homogeneously crushed and mixed to give wettable powder. When in use, this wettable powder is diluted with an appropriate amount of water and applied.

| Formulation Example 5: Flowable (Suspension Concentrate) | |
|---|---|
| Compound No. 4 of the invention | 25 parts |
| Agrisol 8-710 (non-ionic surfactant: trade name supplied by Kao Atlas Co., Ltd., Japan) | 10 parts |
| Lunox 1000C (anionic surfactant: trade name supplied by Toho Chemical Co., Ltd., Japan) | 0.5 part |
| 1% aqueous Rhodopol (thickening agent: trade name supplied by Rhone-Poulenc S.A. | 20 parts |
| Water | 44.5 parts |

The above ingredients are homogeneously mixed to give flowable. When in use, this flowable is diluted with an appropriate amount of water and applied.

| Formulation Example 6: Flowable (Suspension Concentrate) | |
|---|---|
| Compound No. 19 of the invention | 25 parts |
| Agrisol 8-710 (non-ionic surfactant: trade name supplied by Kao Atlas Co., Ltd., Japan) | 10 parts |
| Lunox 1000C (anionic surfactant: trade name supplied by Toho Chemical Co., Ltd., Japan) | 0.5 part |
| 1% aqueous Rhodopol (thickening agent: trade name supplied by Rhone-Poulenc S.A. | 20 parts |
| Water | 44.5 parts |

The above ingredients are homogeneously mixed to give flowable. When in use, this flowable is diluted with an appropriate amount of water and applied.

| Formulation Example 7: Granule | |
|---|---|
| Compound No. 24 of the invention | 5 parts |
| bentonite | 55 parts |
| talc | 40 parts |

After the above ingredients are homogeneously mixed and crushed, a small amount of water is added thereto and the mixture is kneaded well, granulated by means of an extrusion type granulator and dried to give granules.

The herbicidal compositions containing the compounds according to the present invention are applicable to non-cultivation lands such as athletic fields, vacant lands, railroad sides to damage and control a variety of weeds in addition to agricultural and horticultural lands such as farmlands, paddy fields, fruit gardens, etc. The application dosage of the compounds according to the invention may vary depending upon the place to be applied, application season, application manner, kind of weeds to be controlled, cultivated crops, etc., and is generally in the range of 0.025 to 10 kg per hectare (ha).

The herbicidal effectiveness of the compounds according to the present invention will be explained specifically by way of the following test examples.

BIOLOGICAL EXAMPLES

Test Example 1: Herbicidal effect by soil-treatment

Sterilized diluvial soil was placed in a plastic pot of 1/10000 are (a) in opening area and 10 cm in depth. Then were sown in spot-like *Echinochloa crus-galli* (barnyardgrass), *Xanthium strumarium* (cocklebur), *Abutilon theophrasti* (velvet leaf), *Polygonum nodosum* (smartweed), *Amaranthus ascendens* (pigweed) and *Cyperus esculentus* (yellow nutsedge), respectively. After the seeds were covered with the soil about 1.5 cm in depth, a diluted solution containing a predetermined amount of an active ingredient was applied uniformly over the surface of the soil.

The diluted solution was prepared by diluting with water the wettable powder or emulsifiable concentrate in the above formulation examples and applied by means of a small spray over the whole surface of the soil. Four weeks after the application, herbicidal effect against various weeds was evaluated according to the following evaluation rating. The results are shown in Table 3.

Evaluation rating:
5 ... above 90% in herbicidal rate (completely withered)
4 ... 70 to 90% in herbicidal rate
3 ... 40 to 70% in herbicidal rate
2 ... 20 to 40% in herbicidal rate
1 ... 5 to 20% in herbicidal rate
0 ... less than 5% in herbicidal rate (practically no effective)

The above herbicidal rate was calculated according to the following equation by measuring the weight of the living weeds above the soil each in a treated plot and an untreated plot.

$$\text{Herbicidal rate (\%)} = \left(1 - \frac{\text{weight of living weeds above the soil in a treated plot}}{\text{weight of living weeds above the soil in an untreated plot}}\right) \times 100$$

TABLE 3

| Compound No. | Application dosage of an active ingredient (Kg a·i/ha) | Echinochloa crus-galli (barnyardgrass) | Amaranthus ascendens (pigweed) | Polygonum nodosum (smartweed) | Xanthium strumarium (cocklebur) | Abutilon theophrasti (velvet leaf) | Cyperus esculentus (yellow nutsedge) |
|---|---|---|---|---|---|---|---|
| 1 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 2 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 3 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 4 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 5 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 8 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 9 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 10 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 11 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 13 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 14 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 15 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 19 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 20 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 60 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| 83 | 2.0 | 5 | 5 | 5 | 5 | 5 | 5 |
|   | 1.0 | 5 | 5 | 5 | 5 | 5 | 5 |
|   | 0.5 | 5 | 5 | 5 | 5 | 5 | 5 |
| atrazine (control comp.) | 2.0 | 3 | 5 | 5 | 5 | 5 | 2 |
|   | 1.0 | 2 | 5 | 5 | 5 | 5 | 1 |

TABLE 3-continued

| Compound No. | Application dosage of an active ingredient (Kg a · i/ha) | Echinochloa crus-galli (barnyardgrass) | Amaranthus ascendens (pigweed) | Polygonum nodosum (smartweed) | Xanthium strumarium (cocklebur) | Abutilon theophrasti (velvet leaf) | Cyperus esculentus (yellow nutsedge) |
|---|---|---|---|---|---|---|---|
| | 0.5 | 2 | 5 | 5 | 4 | 4 | 0 |
| alachlor (control comp.) | 2.0 | 5 | 3 | 3 | 3 | 3 | 2 |
| | 1.0 | 5 | 2 | 2 | 2 | 2 | 2 |
| | 0.5 | 5 | 2 | 2 | 1 | 2 | 1 |
| Compound B (control comp.) | 2.0 | 2 | 2 | 2 | 1 | 2 | 1 |
| | 1.0 | 1 | 2 | 1 | 1 | 1 | 1 |
| | 0.5 | 0 | 0 | 0 | 0 | 0 | 0 |

Test Example 2: Phytotoxity test against cultivated plants by soil-treatment In a plastic box of 15 cm (length)×22 cm (width)×6 cm (depth) was placed sterilized diluvial soil, and corn and *Sorghum bicolor* (sorghum) were sown. After covering the seeds with the soil about 1.5 cm in depth, a diluted solution containing a predetermined amount of an active ingredient was uniformly applied over the surface of the soil. The diluted solution was prepared by diluting with water the wettable powder or emulsifiable concentrate in the above formulation examples, and the resulting diluted solution was applied by means of a small spray over the whole surface of the soil. Three weeks after the application, phytotoxity against the above crops was evaluated according to the following evaluating rating. The results are shown Table 4.

Evaluation rating:
5 ... crops are almost completely withered.
4 ... remarkable phytotoxity against crops is observed.
3 ... phytotoxity against crops is observed.
2 ... some phytotoxity against crops is observed.
1 ... phytotoxity against crops is scarcely observed.
0 ... no phytotoxity against crops is observed.

TABLE 4

| Compound No. | Application dosage of an active ingredient (Kg a · i/ha) | corn | sorghum |
|---|---|---|---|
| 1 | 5.0 | 0 | 0 |
| | 2.5 | 0 | 0 |
| 2 | 5.0 | 0 | 0 |
| | 2.5 | 0 | 0 |
| 3 | 5.0 | 0 | 0 |
| | 2.5 | 0 | 0 |
| 4 | 5.0 | 0 | 0 |
| | 2.5 | 0 | 0 |
| 5 | 5.0 | 0 | 0 |
| | 2.5 | 0 | 0 |
| 8 | 5.0 | 0 | 0 |
| | 2.5 | 0 | 0 |
| 9 | 5.0 | 0 | 0 |
| | 2.5 | 0 | 0 |
| 10 | 5.0 | 0 | 0 |
| | 2.5 | 0 | 0 |
| 11 | 5.0 | 0 | 0 |
| | 2.5 | 0 | 0 |
| 13 | 5.0 | 0 | 0 |
| | 2.5 | 0 | 0 |
| 14 | 5.0 | 0 | 0 |
| | 2.5 | 0 | 0 |
| 15 | 5.0 | 0 | 0 |
| | 2.5 | 0 | 0 |
| 19 | 5.0 | 0 | 0 |
| | 2.5 | 0 | 0 |
| 20 | 5.0 | 0 | 0 |
| | 2.5 | 0 | 0 |
| 60 | 5.0 | 0 | 0 |
| | 2.5 | 0 | 0 |
| 83 | 5.0 | 0 | 0 |
| | 2.5 | 0 | 0 |
| atrazine (control comp.) | 5.0 | 1 | 2 |
| | 2.5 | 0 | 1 |
| | 1.25 | 0 | 0 |
| alachlor (control comp.) | 5.0 | 1 | 2 |
| | 2.5 | 0 | 1 |

Test Example 3: Herbicidal effect test (1) in submerged conditions

Alluvial soil was placed in a Neubauer pot of 1/10,000 are (a), and water was added thereto to obtain a submerged state of 2 cm in water depth through mixing. A mixture of the seeds of rice plant, *Echinochloa crus-galli* (barnyardgrass), *Monochoria vaginalis* (ducksalad), *Lindernia pyxidaria*, *Rotala indica* (toothcup) and *Scirpus hotarui* (bulrush) was sown in the pot and the tubers of *Sagittaria pygmaea* (arrowhead), *Cyperus serotinus* (perennial flate sedge) and *Eleocharis kuroguwai* (perennial spikerush) were planted and 3.5–4.0 of leaf stage rice plant were transplanted therein. The next day, a diluted solution containing a predetermined amount of an active ingredient was added dropwise over the surface of the water in the pot by means of a measuring pipette. Three weeks after the application, herbicidal effect against the above weeds were evaluated according to the following evaluation rating. The results are shown in Table 5.

Evaluation rating:
5 ... above 90% in herbicidal rate (almost completely withered)
4 ... 70~90% in herbicidal rate
3 ... 40~70% in herbicidal rate
2 ... 20~40% in herbicidal rate
1 ... 5~20% in herbicidal rate
0 ... below 5% in herbicidal rate (practically not effective)

The above herbicidal rate was calculated according to the following equation by measuring the weight of the living weeds above the soil each in a treated plot and an untreated plot.

$$\text{Herbicidal rate (\%)} = \left(1 - \frac{\text{weight of living weeds above the soil in a treated plot}}{\text{weight of living weeds above the soil in an untreated plot}}\right) \times 100$$

TABLE 5

| Compound No. | Application dosage (Kg/ha) | Herbicidal effects | | | | | | | |
|---|---|---|---|---|---|---|---|---|---|
| | | Rice plant | Echinochloa crus-galli | Monochoria vaginalis | Lindernia pyxidaria | Rotala indica | Scirpus hotarui | Sagittaria pygmaea | Cyperus serotinus | Eleocharis kurogwai |
| 1 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 5 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 6 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 7 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 8 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 10 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 11 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 13 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 14 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 15 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 16 | 0.5 | 0 | 5 | 5 | 5 | 5 | 5 | 5 | 5 | 5 |
| | 0.25 | 0 | 4 | 5 | 5 | 5 | 5 | 5 | 5 | 5 |
| | 0.125 | 0 | 3 | 5 | 5 | 5 | 5 | 5 | 5 | 5 |
| 17 | 0.5 | 0 | 5 | 5 | 5 | 5 | 5 | 5 | 5 | 5 |
| | 0.25 | 0 | 4 | 5 | 5 | 5 | 5 | 5 | 5 | 5 |
| | 0.125 | 0 | 3 | 5 | 5 | 5 | 5 | 5 | 5 | 5 |
| 18 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 20 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 21 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 22 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 23 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 24 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 25 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 26 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| 27 | 0.5 | 0 | 5 | 5 | 5 | 5 | 5 | 5 | 5 | 5 |
| | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| Compound A (control comp.) | 0.5 | 0 | 4 | 4 | 4 | 3 | 3 | 4 | 3 | 2 |
| | 0.25 | 0 | 3 | 3 | 3 | 2 | 2 | 2 | 2 | 1 |
| | 0.125 | 0 | 2 | 2 | 1 | 1 | 1 | 1 | 1 | 0 |
| Compound B (control comp.) | 0.5 | 0 | 3 | 3 | 3 | 3 | 2 | 4 | 1 | 0 |
| | 0.25 | 0 | 2 | 2 | 2 | 2 | 1 | 2 | 0 | 0 |
| | 0.125 | 0 | 1 | 1 | 1 | 1 | 0 | 1 | 0 | 0 |

Test Example 4: Herbicidal effect test (2) in submerged conditions

Alluvial soil was placed in a Wagner pot of 1/5,000 are (a), and water was added thereto to obtain a submerged state of 2 cm in water depth through mixing. In the submerged soil in the Wagner pot were planted the tubers of *Cyperus serotinus* (perennial flat sedge) and *Eleocharis kuroguwai* (perennial spikerush) which had been picked in the previous year from a paddy field in which perennial weeds frequently occur and the seeds of *Scirpus hotarui* (bulrush) were scattered. Soon after germination of the weeds took place, a diluted solution of an active ingredient was added dropwise by means of a measuring pipette over the surface of the water in the pot to apply a predetermined amount of the active ingredient. Three weeks after the application, the weights of living weeds were measured and herbicidal rates (%) were calculated. Incidentally, the whitened portions of the weeds were regarded as withered portions. The results are shown in Table 6.

Herbicidal rate (%) =

$$\left(1 - \frac{\text{weight of living weeds above the soil in a treated plot}}{\text{weight of living weeds above the soil in an untreated plot}}\right) \times 100$$

TABLE 6

| Compound No. | Application dosage of an active ingredient (Kg a · i/ha) | Scirpus hotarui | Cyperus serotinus | Eleocharis kuroguwai |
|---|---|---|---|---|
| 1 | 0.5 | 100 | 100 | 100 |
|   | 0.25 | 100 | 100 | 100 |
|   | 0.125 | 100 | 100 | 100 |
| 2 | 0.5 | 100 | 100 | 100 |
|   | 0.25 | 100 | 100 | 100 |
|   | 0.125 | 100 | 100 | 100 |
| 3 | 0.5 | 100 | 100 | 100 |
|   | 0.25 | 100 | 100 | 100 |
|   | 0.125 | 100 | 100 | 100 |
| 4 | 0.5 | 100 | 100 | 100 |
|   | 0.25 | 100 | 100 | 100 |
|   | 0.125 | 100 | 100 | 100 |
| 5 | 0.5 | 100 | 100 | 100 |
|   | 0.25 | 100 | 100 | 100 |
|   | 0.125 | 100 | 100 | 100 |
| 6 | 0.5 | 100 | 100 | 100 |
|   | 0.25 | 100 | 100 | 100 |
|   | 0.125 | 100 | 100 | 100 |
| 7 | 0.5 | 100 | 100 | 100 |
|   | 0.25 | 100 | 100 | 100 |
|   | 0.125 | 100 | 100 | 100 |
| 8 | 0.5 | 100 | 100 | 100 |
|   | 0.25 | 100 | 100 | 100 |
|   | 0.125 | 100 | 100 | 100 |
| 9 | 0.5 | 100 | 100 | 100 |
|   | 0.25 | 100 | 100 | 100 |
|   | 0.125 | 100 | 100 | 100 |
| 10 | 0.5 | 100 | 100 | 100 |
|   | 0.25 | 100 | 100 | 100 |
|   | 0.125 | 100 | 100 | 100 |
| 11 | 0.5 | 100 | 100 | 100 |
|   | 0.25 | 100 | 100 | 100 |
|   | 0.125 | 100 | 100 | 100 |
| 13 | 0.5 | 100 | 100 | 100 |
|   | 0.25 | 100 | 100 | 100 |
|   | 0.125 | 100 | 100 | 100 |
| 14 | 0.5 | 100 | 100 | 100 |
|   | 0.25 | 100 | 100 | 100 |
|   | 0.125 | 100 | 100 | 100 |
| 15 | 0.5 | 100 | 100 | 100 |
|   | 0.25 | 100 | 100 | 100 |
|   | 0.125 | 100 | 100 | 100 |
| 16 | 0.5 | 100 | 100 | 100 |
|   | 0.25 | 100 | 100 | 100 |
|   | 0.125 | 100 | 100 | 100 |
| 17 | 0.5 | 100 | 100 | 100 |
|   | 0.25 | 100 | 100 | 100 |
|   | 0.125 | 100 | 100 | 100 |
| 18 | 0.5 | 100 | 100 | 100 |
|   | 0.25 | 100 | 100 | 100 |
|   | 0.125 | 100 | 100 | 100 |
| 19 | 0.5 | 100 | 100 | 100 |
|   | 0.25 | 100 | 100 | 100 |
|   | 0.125 | 100 | 100 | 100 |
| 20 | 0.5 | 100 | 100 | 100 |
|   | 0.25 | 100 | 100 | 100 |
|   | 0.125 | 100 | 100 | 100 |
| 21 | 0.5 | 100 | 100 | 100 |
|   | 0.25 | 100 | 100 | 100 |
|   | 0.125 | 100 | 100 | 100 |
| 22 | 0.5 | 100 | 100 | 100 |
|   | 0.25 | 100 | 100 | 100 |
|   | 0.125 | 100 | 100 | 100 |
| 23 | 0.5 | 100 | 100 | 100 |
|   | 0.25 | 100 | 100 | 100 |
|   | 0.125 | 100 | 100 | 100 |
| 24 | 0.5 | 100 | 100 | 100 |
|   | 0.25 | 100 | 100 | 100 |
|   | 0.125 | 100 | 100 | 100 |
| 25 | 0.5 | 100 | 100 | 100 |
|   | 0.25 | 100 | 100 | 100 |
|   | 0.125 | 100 | 100 | 100 |
| 26 | 0.5 | 100 | 100 | 100 |
|   | 0.25 | 100 | 100 | 100 |
|   | 0.125 | 100 | 100 | 100 |
| 27 | 0.5 | 100 | 100 | 100 |
|   | 0.25 | 100 | 100 | 100 |
|   | 0.125 | 100 | 100 | 100 |
| 60 | 0.5 | 100 | 100 | 100 |
|   | 0.25 | 100 | 100 | 100 |
|   | 0.125 | 100 | 100 | 100 |
| 83 | 0.5 | 100 | 100 | 100 |
|   | 0.25 | 100 | 100 | 100 |
|   | 0.125 | 100 | 100 | 100 |
| Compound A (control comp.) | 0.5 | 65 | 58 | 25 |
|   | 0.25 | 28 | 25 | 10 |
|   | 0.125 | 11 | 10 | 0 |
| Compound B (control comp.) | 0.5 | 48 | 38 | 8 |
|   | 0.25 | 23 | 12 | 0 |
|   | 0.125 | 8 | 0 | 0 |

The control compounds used in Test Examples 1 through 4 have the following structural formula:

atrazine:

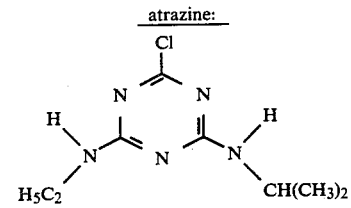

alachlor:

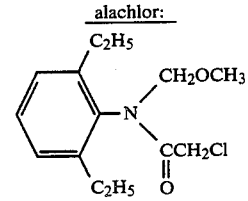

Compound A:

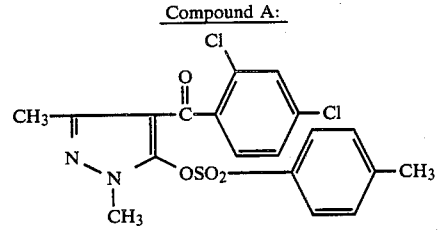

Compound B:

-continued

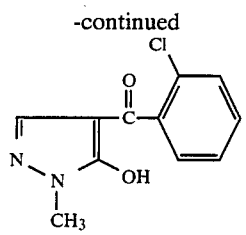

(a compound described in Japanese Patent Publication No. Sho 54-36648).

What is claimed is:

1. A compound of the formula:

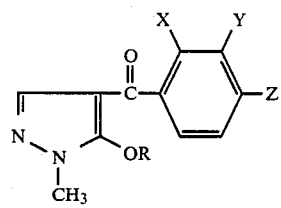

(I)

wherein,
X denotes a halogen, nitro or methanesulfonyl,
Y denotes hydrogen, a lower alkyl or a halogen,
Z denotes methanesulfonyl, and
R denotes hydrogen; an organic acid residue selected from the group consisting of methanesulfonyl, p-toluenesulfonyl, benzoyl, tert-butoxycarbonyl, acetyl, cyclohexylcarbonyl, cinnamoyl, acryloyl, phenoxyacetyl, ethoxycarbonyl, N,N-dimethylcarbamoyl, N,N-dimethylsulfamoyl, benzenesulfonyl, trifluoromethanesulfonyl, diethylphosphoryl and diethylthiophosphoryl; a lower alkynyl; a lower alkyl or a lower alkenyl which may be substituted by a halogen, hydroxy, cyano or an alkoxycarbonyl; or a benzyl which may be substituted by a halogen, nitro or a lower alkyl.

2. A compound of the formula:

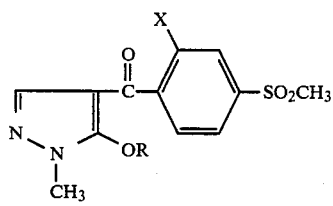

wherein, X denotes a halogen, and R denotes hydrogen; an organic acid residue; a lower alkyl; a lower alkenyl; a lower alkynyl; a lower alkyl or lower alkenyl each substituted by a halogen, hydroxy, cyano or alkoxycarbonyl; or a benzyl which may be substituted by a halogen, nitro or a lower alkyl.

3. A compound of the formula:

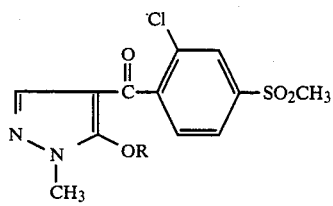

wherein, R denotes hydrogen, methanesulfonyl or p-toluenesulfonyl.

4. A compound of claim 1 having the formula:

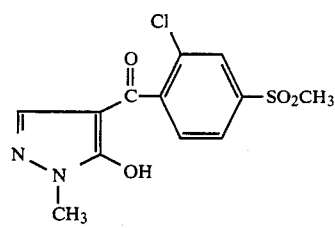

5. A compound of claim 1 having the formula:

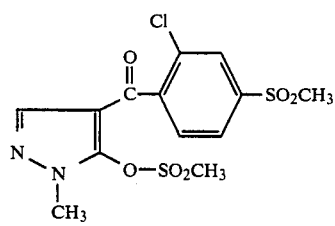

6. A compound of claim 1 having the formula:

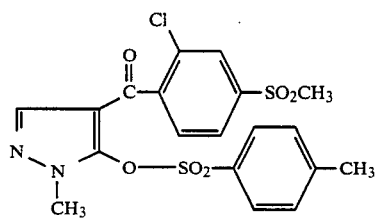

7. A compound of claim 1 having the formula:

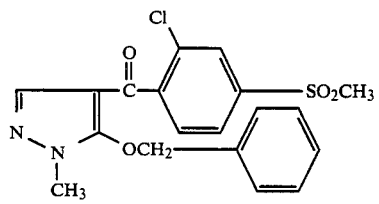

8. A compound of claim 1 having the formula:

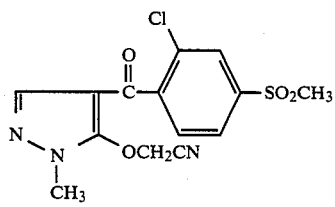

9. A compound of claim 1 having the formula:

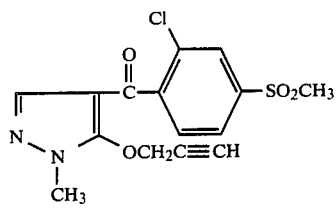

10. A selective herbicidal composition containing as an active ingredient an effective amount of one or more of the compounds of claim 1 of the formula I:

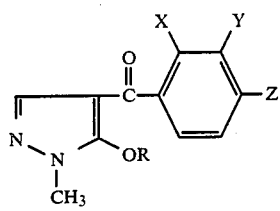

(I)

wherein,

X denotes a halogen, nitro or methanesulfonyl,

Y denotes hydrogen, a lower alkyl or a halogen,

Z denotes methanesulfonyl, and

R denotes hydrogen; an organic acid residue selected from the group consisting of methanesulfonyl, p-toluenesulfonyl, benzoyl, tert-butoxycarbonyl, acetyl, cyclohexylcarbonyl, cinnamoyl, acryloyl, phenoxyacetyl, ethoxycarbonyl, N,N-dimethylcarbamoyl, N,N-dimethylsulfamoyl, benzenesulfonyl, trifluorometthanesulfonyl, diethylphosphoryl and diethylthiophosphoryl; a lower alkynyl; a lower alkyl or a lower alkenyl which may be substituted by a halogen, hydroxy, cyano or an alkoxycarbonyl; or a benzyl which may be substituted by a halogen, nitro or a lower alkyl; together with an inert carrier therefor.

11. A selective herbicidal composition containing as an active ingredient an effective amount of one or more of the compounds of the formula:

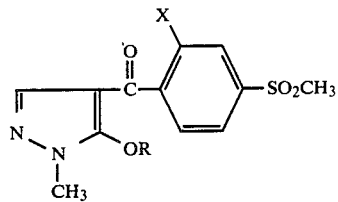

wherein, X denotes a halogen, and R denotes hydrogen; an organic acid residue; a lower alkynyl; a lower alkyl or lower alkenyl which may be substituted by a halogen, hydroxy, cyano or an alkoxycarbonyl; or a benzyl which may be substituted by a halogen, nitro or a lower alkyl, together with an inert carrier therefor.

12. A method of damaging and controlling weeds in a corn field or sorghum field which comprises applying to the field a selective herbicidal composition containing as an active ingredient one or more of the compounds of claim 1 of the formula I:

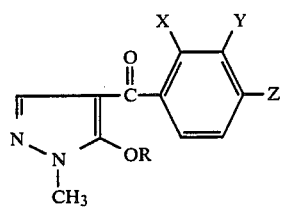

(I)

wherein,

X denotes a halogen, nitro or methanesulfonyl,

Y denotes hydrogen, a lower alkyl or a halogen,

Z denotes methanesulfonyl, and

R denotes hydrogen; an organic acid residue selected from the group consisting of methanesulfonyl, p-toluenesulfonyl, benzoyl, tert-butoxycarbonyl, acetyl, cyclohexylcarbonyl, cinnamoyl, acryloyl, phenoxyacetyl, ethoxycarbonyl, N,N-dimethylcarbamoyl, N,N-dimethylsulfamoyl, benzenesulfonyl, trifluoromethanesulfonyl, diethylphosphoryl and diethylthiophosphoryl; a lower alkynyl; a lower alkyl or a lower alkenyl which may be substituted by a halogen, hydroxy, cyano or an alkoxycarbonyl; or a benzyl which may be substituted by a halogen, nitro or a lower alkyl; together with an inert carrier therefor in an amount of 0.025 to 10 kg per hectare (ha) of the active ingredient.

* * * * *